United States Patent [19]

Woods et al.

[11] Patent Number: 4,732,956
[45] Date of Patent: Mar. 22, 1988

[54] STYRYLOXY RESINS AND COMPOSITIONS THEREOF

[75] Inventors: John Woods, Dublin; John Rooney, Kildare; Stephen J. Harris, Dublin, all of Ireland

[73] Assignee: Loctite (Ireland) Ltd., Dublin, Ireland

[21] Appl. No.: 779,737

[22] Filed: Sep. 24, 1985

Related U.S. Application Data

[63] Continuation-in-part of Ser. No. 667,724, Dec. 4, 1984, Pat. No. 4,543,397, which is a continuation-in-part of Ser. No. 621,419, Jun. 18, 1984, abandoned.

[51] Int. Cl.$^4$ .................. C08F 283/04; C07D 211/26
[52] U.S. Cl. .................................. 526/260; 548/229; 528/75; 525/455; 526/263
[58] Field of Search ................. 548/229; 525/455; 528/75; 526/260, 263

[56] References Cited

U.S. PATENT DOCUMENTS

| | | | |
|---|---|---|---|
| 4,062,862 | 12/1977 | Fujimoto et al. | 548/229 |
| 4,250,318 | 2/1981 | Dosert et al. | 548/229 |
| 4,543,397 | 9/1985 | Woods et al. | 526/301 |

OTHER PUBLICATIONS

Chem. Abstracts, vol. 60, entry 10664e, Irikura et al.
Chem. Abstracts, vol. 62, entry 14645c, Erescenzi et al.

*Primary Examiner*—Edward J. Smith
*Assistant Examiner*—Peter F. Kulkosky
*Attorney, Agent, or Firm*—Eugene F. Miller; Walter J. Steinkraus; Edward K. Welch, II

[57] ABSTRACT

Polyfunctional cationically polymerizable styryloxy compound of the formula

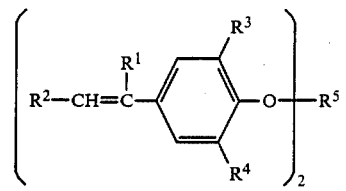

or

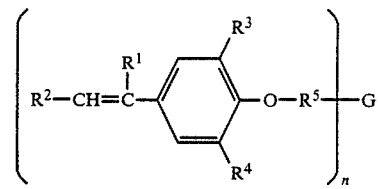

where $R^1$ and $R^2$ are H, or one of $R^1$ and $R^2$ are H and the other is methyl; $R^3$ and $R^4$ are H, lower alkyl, or alkoxy if $R^2$ is not methyl; $R^5$ is a divalent hydrocarbon radical; G is any multivalent organic or inorganic radical free of amino, aliphatic hydroxyl, aliphatic thiol or other groups which interfere with cationic polymerization; and n is an integer of two or more.

2 Claims, No Drawings

STYRYLOXY RESINS AND COMPOSITIONS THEREOF

This application is a continuation-in-part of Ser. No. 677,724 filed Dec. 4, 1984, now U.S. Pat. No. 4,543,397, which is a continuation in part of Ser. No. 621,419, filed June 18, 1984, now abandoned.

FIELD OF THE INVENTION

It is an object of the present invention to provide a new class of polymerizable monomers which are polyfunctional, so as to be cured to cross-linked high molecular weight polymer networks, and which are readily cationically polymerizable.

BACKGROUND OF THE INVENTION

In USSR Pat. Nos. 443874 and 478026 there are described ion exchange polymers prepared by free radical copolymerization of styrene or maleic anhydride, respectively, with p-glycidoxy-α-methyl styrene (I)

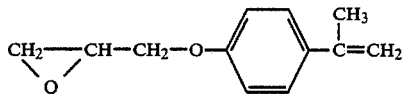

In U.S. Pat. No. 3,327,019 there are described diethers which are the reaction product of p-glycidoxy styrenes and polyols. These compounds include aliphatic hydroxyl groups.

In *Macromolecules*, 16, 510–517(1983), there is described the cationic polymerization of p-methoxy and p-(ethoxymethoxy)-α-methyl styrenes with boron trifluoride etherate as initiator in dichloromethane. These polymers are then subjected to ether cleavage reactions to yield linear polymers containing pendant phenolic groups.

It is known from kinetic studies of the cationic polymerization of p-methoxy styrene that this monomer has a very high rate of polymerization. See, e.g., *Macromolecules*, 9, 931–936(1976); and *Polymer*, 16, 819–826(1975).

SUMMARY OF THE INVENTION

The present invention is directed to a new class of cationic polymerizable monomers. In common with the monofunctional monomers discussed above, the inventive monomers contain styryloxy (p-vinylphenol ether) functionality. They are represented by the formulas:

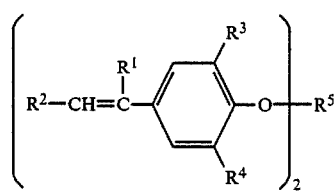

or

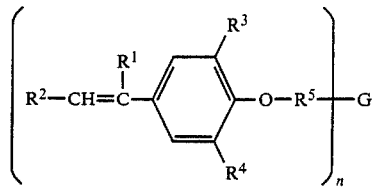

where $R^1$ and $R^2$ are H, or one of $R^1$ and $R^2$ are H and the other is methyl; $R^3$ and $R^4$ are H, lower alkyl, or alkoxy if $R^2$ is not methyl; $R^5$ is a divalent hydrocarbon radical; G is any multivalent organic or inorganic radical free of amino, aliphatic thiol, aliphatic hydroxyl, or other groups which interfere with cationic polymerization; and n is an integer of two or more.

In addition to high reactivity to cationic polymerizations, the inventive monomers have been shown to develop an intense coloration when they are polymerized by UV irradiation in the presence of acid generating photoinitiators. Under some circumstances this coloration is sufficient to mask a substrate, providing a useful means of generating opacity in photocurable coatings. This coloration is also observed in chemically initiated cationic polymerizations of these materials.

An additional feature of solid polyfunctional styryloxy resins of the invention is an ability of these resins to cure by UV irradiation without added photoinitiator. This cure is believed to involve a radical mechanism.

DETAILED DESCRIPTION OF THE INVENTION

The inventive monomers may readily be prepared from p-vinyl phenols, p-propenyl phenols or p-isopropenyl phenols by a variety of methods such as etherification with an appropriate multifunctional etherifying agent, or reaction with multifunctional epoxies followed by reaction of the resulting aliphatic hydroxyl with a polyisocyanate or other suitable capping agent.

A suitable p-vinyl phenol is the commercially available vinyl guaiacol (2-methoxy-4-vinyl phenol). Synthetic methods for obtaining other suitable phenols include those reported in U.S. Pat. No. 3,327,019, column 3, line 38–column 4, line 2; Japanese Kokai Tokkyo Koho 79: 55, 529 (dehydrogenation of ethyl phenol to give vinyl phenol); J. Kahovec, et al., *J. Collect. Czech. Chem. Commun.*, 36, 1986(1971) (various α-methylvinyl phenols); and *Macromolecules*, 16 510–517 (1983)(p-hydroxy-α-methyl styrene by cleavage of 2,2-bis(p-hydroxyphenyl)-propane), the disclosures of which are incorporated herein by reference.

Yet another synthetic procedure involves the modification of the procedure of *Macromolecules*, 16, 510–517 (1983), in which p-(ethoxymethoxy)-α-methyl styrene is prepared from p-hydroxyacetophenone by etherifying the hydroxyl group and then using a Wittig reaction on the resulting p-(ethoxymethoxy) acetophenone. One modification required for the synthesis of the inventive monomers is the initial reaction of p-hydroxyacetophenone with an appropriate polyfunctional etherification reagent to form a molecule having multi-acetophenone functionalities. Subjecting such a molecule to a Wittig reaction as in the Macromolecules reference will yield a polyfunctional monomer of the invention.

An alternative modification of the Wittig reaction procedure is to use a monofunctional etherification reagent which is capable of entering into subsequent chain extension reactions with polyfunctional moieties. An example is etherification of p-hydroxyacetophenone with allyl bromide, Wittig reaction to give the corresponding allyloxy styrene and hydrosilation using a silicone resin with poly Si—H functionality.

In the formulas (II) and (III) above, it is generally preferred that $R^3$ is H, methyl, or methoxy and $R^4$ is H. However, other lower alkyl or alkoxy (up to about $C_4$) may be included as substituents $R^3$ and/or $R^4$).

Examples of $R^5$ groups are methylene, ethylene or cycloaliphatic, aromatic hydrocarbons such as 1,4-dimethylenebenzene or unsaturated linear hydrocarbons such as propenylene or butenylene.

The only limitation on G is that it must not interfere with cationic polymerization of the styryloxy groups. G must not include any strongly electron withdrawing group in conjugation with the styryloxy group oxygen atom as such groups will interfere with vinyl cationic polymerizations. Amines, aliphatic hydroxyls, and aliphatic thiols are known to prevent or slow vinyl cationic polymerizations. "Developments in Polymerization -1," R. N. Howard ed., Applied Science Publishers, 1979, pg. 80. Inclusion of these groups in G should therefore also be avoided.

Polymerization of the inventive monomers may be accomplished by conventional acid and Lewis acid cationic initiators such as methane sulfonic acid, toluene sulfonic acid and boron trifluoride etherate. UV cationic initiators may also be used. Such UV cationic photointiators include salts of a complex halogenide having the formula:

$[A]_d^+[MX_e]^{-(e-f)}$, where A is a cation selected from the group consisting of iodonium, sulfonium, pyrylium, thiopyrylium and diazonium cations, M is a metalloid, and X is a halogen radical, b equals e minus f, f equals the valance of M and is an integer equal to from 2 to 7 inclusive, e is greater than f and is an integer having a value up to 8. Examples include di-p-tolyl iodonium hexafluorophosphate, diphenyl iodonium hexafluorophosphate, diphenyl iodonium hexafluoroarsenate and UVE 1014 (trademark of General Electric), a commercially available sulfonium salt of a complex halogenide.

Certain monomers, usually solids, will also undergo UV initiated polymerization in the solid state without initiator, yielding an essentially uncolored product. A radical mechanism is believed to be involved. This UV, initiator free, polymerization has also been obtained with a liquid silicone backbone resin of the invention.

The production of colored reaction mixtures by cationic initiators has been reported before for styryloxy monomers. Permanent coloration in the cured products of the invention is believed to result from particular termination reactions involving stable carbocations. The development of color can thus be controlled by selecting polymerization conditions designed to select for or against termination by stable carbocations. The development of permanent color as a result of polymerization termination reactions is especially advantageous at certain UV cured opaque coating applications where the use of pigments or dyes in the composition blocks UV, resulting in only surface cure of the coating. Since the inventive resins develop their intense coloration only after initiation of polymerization, initation by UV is not interfered with. The invention may be illustrated by reference to the following nonlimiting examples:

EXAMPLE 1

To a mixture of 3.0 grams vinyl guaiacol, 27.0 grams ethanol, 30 grams acetone and 20 grams potassium carbonate stirred in a round-bottom flask was added, dropwise over 30 minutes, a solution of 2.8 grams $\alpha,\alpha'$-dibromo-p-xylene in 30 grams acetone. The resulting mixture was stirred at room temperature for 24 hours. The potassium carbonate was then filtered off and the solvent removed under reduced pressure. The residue was redissolved in chloroform (250 ml) and extracted with distilled water (3×100 ml). The chloroform layer was then dried over sodium sulfate and filtered. Solvent was removed under reduced pressure and the residue was recrystallized from hot ethanol to yield 2.01 grams slightly yellow crystals. This material was identified from proton NMR (CDCl$_3$; $\delta$=3.87, singlet, methoxy protons; $\delta$=5.05, 5.22. 5.45 and 5.74 quartet, $\beta$-vinyl protons; $\delta$=5.12, singlet, benzyl protons; $\delta$=6.44–7.2 multiplet, $\alpha$-vinyl and guaiacol ring protons; $\delta$=7.45, singlet, xylene ring protons) and IR (3085 cm$^{-1}$: vinyl C—H; 3010 cm$^{-1}$: aryl-H; 2860 cm$^{-1}$: methoxy C—H; 1625 cm$^{-1}$ conjugated c=c; 1140 cm$^{-1}$: aromatic-O; 1030 cm$^{-1}$: alkyl C-O-aromatic; 995 and 900 cm$^{-1}$: R—CH=CH$_2$; 860 cm$^{-1}$: 2 adjacent aromatic C—H) spectra as $\alpha,\alpha'$-bis(2-methoxy-4-vinylphenoxy)-p-xylene.

EXAMPLE 2

A mixture of 5.0 grams vinyl guaiacol, 3.47 grams allyl glycidyl ether, 45 grams ethanol, 0.68 grams of a commercially available ion exchange resin (Rohm and Haas Amberlyst A-27) and 0.80 grams benzyl trimethyl ammonium hydroxide was heated for 65 hours at reflux. The mixture was then filtered and solvent was removed under reduced pressure. The residue was chromatographed on a silica gel column using chloroform as the eluent, yielding 6.8 grams of a slightly orange viscous material which was identified by proton NMR and IR spectra as the adduct of vinyl guaiacol and allyl glycidyl ether.

A mixture of this adduct (2.64 grams), a commercially available polyfunctional isocyanate resin (Bayer Desmodur L-75) (2.92 grams), 0.06 grams stannous octoate, and 20 grams chloroform was heated at reflux for 90 minutes under nitrogen. At the end of this time infrared analysis indicated that all of the isocyanate groups had been consumed. After solvent was evaporated, the crude product was washed in a soxhlet extractor and dried in a vacuum desiccator to yield 2.44 grams of product. This product was shown by liquid chromatography, NMR and IR spectroscopy to be a high molecular weight resin containing styryloxy functional groups.

EXAMPLE 3

A solution of 0.120 grams of the $\alpha,\alpha'$-bis(2-methoxy-4-vinylphenoxy)-p-xylene prepared in Example 1 and 0.010 grams of a commercially available cationic sulfonium salt photoinitiator (GE UVE-1014) in 1.000 gram chloroform was coated onto a glass slide and the solvent allowed to evaporate. The coating was then irradiated under a medium-pressure mercury lamp at an intensity of 70 mw/cm$^2$ for 20 seconds, producing a tack-free brittle film with an intense purple coloration. The irradiated film was effective at obscuring the contrast on a Morest chart #05. The irradiated material was insoluble in common organic solvents.

EXAMPLE 4

A solution of 0.100 grams of the styryloxy resin prepared in Example 2 and 0.006 grams of ditolyliodonium hexafluorophosphate in 0.100 grams of anisole was coated onto a glass slide and irradiated under a medium-pressure mercury lamp at an intensity of 60 mw/cm$^2$ for 5 seconds. The film was tack free after irradiation and insoluble in common organic solvents.

EXAMPLE 5

A dilute solution of the α,α'-bis(2-methoxy-4-vinyl-phenoxy)-p-xylene synthesized in Example 1 was prepared by dissolving 0.4022 grams of this material in 50 milliliters of dry dichloromethane. To this solution was added, with stirring, 10 milliliters of a solution prepared by dissolving 0.0574 grams of triphenylcarbenium hexachloroantimonate in 100 milliliters of dry dichloromethane. The reaction mixture developed a red color rapidly and was stirred for three hours at room temperature. The mixture was then added to 50 milliliters of methanol to quench the reaction. Solvents were removed under reduced pressure yielding 0.395 grams of a pink solid polymer. The polymer was dissolved in hot dichloromethane and absolute alcholol was added gradually. On cooling a white precipitate formed. Solvents were removed under reduced pressure yielding 0.352 grams of material. This material was dissolved in tetrahydrofuran and analyzed on a Waters Model 244 Liquid Chromatograph fitted with one 1000 angstrom and two 100 angstrom columns. The material was found to be a high polymer with a peak molecular weight corresponding to 6,500 on a polystyrene calibration.

EXAMPLE 6

To a mixture of 20 grams vinyl guaiacol, 180 grams ethanol, 300 grams acetone and 65.6 grams potassium carbonate was added dropwise over 20 minutes 22.27 grams of ethyl bromoacetate. The color of the mixture changed gradually from green to light brown. The mixture was heated at 45° C. for two hours, then cooled to room temperature and left for a further sixteen hours. Thin-layer chromatography on a sample of the reaction mixture showed the presence of vinyl guaiacol after this time. Consequently, the mixture was heated to reflux for 7 hours and left at room temperature for a further 64 hours. The mixture was then filtered and solvents were removed under vacuum. When 350 grams of solvent had been removed, a precipitate formed in the mixture. The precipitate (3.84 g.) was removed by filtration. The remaining material was distilled into three fractions and a residue (4.32 g, 4.91 g, 1.48 g, and 11 g respectively). Gas-liquid chromatographic analysis of the second fraction showed that it consisted principally (85%) of the adduct of ethyl bromoacetate and vinyl guaiacol, 3-methoxy-4-(2-oxo-2-ethoxy)-ethoxy styrene. The adduct was characterized by NMR (CDCl$_3$; δ=1.27, triplet, ester methyl protons; δ=3.91, singlet, methoxy protons; δ=4.3, quartet, ester methylene protons; δ=4.72, singlet, ether methylene protons; δ=5.1, 5.3, 5.5, and 5.8, quartet, β-vinyl protons; δ=6.5-7.1, multiplet, α-vinyl and ring protons). The remainder of the second fraction (15%) consisted of vinyl guaiacol.

Material from the second fraction (4.0 grams), 1,6-hexanediol (1.0 gram) and lithium ethylene glycolate (0.05 gram) were refluxed in dry heptane for 3 hours. The heptane was removed by distillation to yield 4.73 grams of product. The product was analyzed by liquid chromatography and shown to consist of approximately equal portions of unreacted 3-methoxy-4-(2-oxo-2-ethoxy)ethoxy styrene (MOES), the monofunctional product of the transesterification of MOES and 1,6-hexanediol, and the difunctional product of the transesterification of MOES and 1,6-hexanediol.

A concentrated solution of this product mixture was prepared by dissolving 0.45 grams of the material in 0.65 grams dry dichloromethane. When one drop of methanesulfonic acid was added to the solution the material polymerized instantly to give a red, insoluble product.

EXAMPLE 7

To a solution of 136 g 4-hydroxyacetophenone in 500 mls acetone was added 276.41 g potassium carbonate. This mixture was stirred for 15 minutes. A solution of 133 g allyl bromide in 200 mls acetone was then added dropwise over 45 minutes, and the resulting mixture was stirred for a further 4 hours and left standing for a further 16 hours. Thin-layer chromatography showed some starting material to be present at the end of this time. The mixture was then heated to reflux for 4 hours and left standing a further 16 hours. After filtration the solvent was removed by distillation leaving 230 g of a brown liquid. This residue was distilled under reduced pressure (B.Pt. 107°–115° C. at 0.6 mmHg.) to yield 158 g of pale yellow liquid which was identified by infrared and n.m.r. spectroscopy as 4-allyloxyacetophenone.

To a solution of 5.58 g potassium metal in tert-butanol was added 51 g methyl triphenylphosphonium bromide. The resulting yellow suspension was stirred for 20 minutes. A solution of 18.86 g 4-allyloxyacetophenone in 30 mls tert-butanol was then added gradually and stirred for 16 hours at room temperature. After this time, the mixture was filtered and solvent removed under reduced pressure. The resulting mixture was extracted with petroleum ether to yield 28 g of brown resin. This resin was distilled under reduced pressure (B.Pt. 88° C. at 1 mm Hg) yielding 15.21 g of a clear colorless liquid which was identified by infrared and n.m.r. spectroscopy as 4-allyloxy isopropenyl benzene (Proton NMR: (CDCl$_3$) δ=2.12 singlet, α-methyl protons; δ=4.50, 4.58, doublet, allyloxy methylene protons; δ=5.0-6.5, multiplets, allyl and vinyl group protons; δ=6.80, 6.95, 7.35 and 7.50, quartet, aromatic protons).

A solution of 13.92 g 4-allyloxy isopropenyl benzene in 50.0 g toluene was stirred for 5 minutes at room temperature. To this solution was added 0.693 g of a 2% solution of dihydrogen hexachloroplatinate hexahydrate in n-butyl acetate. The resulting solution was then heated to 80° C. and 40.40 g of a difunctional Si-H terminated polydimethylsiloxane resin of molecular weight 1010 was added gradually over 90 minutes. At the end of that time infrared spectroscopy showed that the peak at 2130 cm$^{-1}$ had disappeared indicating complete consumption of the Si—H groups. Solvent was then removed under reduced pressure to yield 55.78 g of a light brown low viscosity liquid.

Reaction of 1 gram of this product with 0.02 grams methanesulfonic acid led to rapid formation of a rubbery gel insoluble in common organic solvents.

EXAMPLE 8

A mixture of 20.0 g 4-hydroxy-3-methoxy styrene, 27.5 g potassium carbonate and 180 grams ethanol was heated to 40° C. and 17.7 g allyl bromide adddded gradually as a 50% solution in ethanol. The mixture was stirred for two hours at 55°–65° C. The solids were then filtered and solvent removed under reduced pressure. The remaining liquid was then distilled under reduced pressure (B.Pt. 96°–108° C. at 0.2 mmHg) to yield 13.2 g of clear liquid identified by infrared and n.m.r. spectroscopy as 4-allyloxy-3-methoxystyrene (Proton NMR: (CDCl$_3$) $\delta$=3.87, singlet, methoxy protons; $\delta$=4.55, 4.62, doublet, allyloxy methylene protons; $\delta$=5.05–7.1, multiplets, vinyl, allyl and aromatic protons.

To a solution of 9.5 g 4-allyloxy-3-methoxy styrene in 34.75 g toluene was added 0.459 g of a 2% solution of dihydrogen hexachloroplatinate hexahydrate in n-butyl acetate. The resulting solution was then heated to 80° C. and 25.3 g of a difunctional Si—H terminated polydimethylsiloxane resin of molecular weight 1010 was added gradually over 30 minutes. At the end of that time infrared spectroscopy showed that the peak at 2130 cm$^{-1}$ had disappeared indicating complete consumption of the Si—H groups. Solvent was then removed under reduced pressure to yield 32.97 g of a clear colorless resin.

Reaction of 0.5 gram of this product with 0.02 gram methane sulfonic acid led to rapid formation of a rubbery purple gel which was insoluble in common organic solvents.

EXAMPLE 9

An aliquot of the difunctional styryloxy silicone resin synthesized in Example 2 was blended with 3% by weight of a commercially available triarylsulfonium salt photoinitiator (UVE-1014, trademark of General Electric). A drop of this formulation was placed on a glass slide and irradiated under a medium-pressure mercury lamp at an intensity of about 100 mw/cm$^2$ at 365 nm for 10 seconds. At the end of this time the formulation had completely cured to a rubbery tack-free film. Irradiation for 30 seconds led to formation of a purple rubbery tack-free film.

EXAMPLE 10

To a solution of 122 g 4-hydroxybenzaldehyde in 500 mls acetone was added 276 g potassium carbonate. This mixture was stirred for 15 minutes. A solution of 133 g allyl bromide in 200 mls acetone was then added dropwise over 30 minutes. The resulting mixture was heated at reflux for 1 hours, left standing for a further 16 hours and finally heated at reflux for 2 hours. After filtration, the solvent was removed by distillation leaving 175 g of a reddish liquid. This residue was distilled under reduced pressure (B.Pt. 104°–114° C. at 1.5 mmHg) to yield 130 g of a pale yellow liquid which was identified by infrared and n.m.r. spectroscopy as 4-allyloxybenzaldehyde.

To a solution of 9.36 g potassium metal in 500 mls tert-butanol was added 85.68 g methyltriphenylphosphonium bromide. The resulting yellow suspension was stirred for 20 minutes and 32.4 g 4-allyloxybenzaldehyde was then added over 10 minutes. This mixture was stirred for 30 minutes and then allowed to stand overnight. After filtration the solvent was removed under reduced pressure leaving 107 g of a red semi-solid residue. Petroleum ether (B.Pt. 40°–60° C.) was added to the residue precipitating a solid which was filtered. After removal of the petroleum ether, the remaining resin was distilled under reduced pressure (B.Pt. 68°–82° C. at 0.4 mmHg) yielding 26.7 g of a clear colorless liquid which was identified by infrared and n.m.r. spectroscopy as 4-allyloxystyrene (Proton NMR: (CDCl$_3$) $\delta$=4.50, 4.58, doublet, allyloxymethylene protons; $\delta$=5.0–6.5, multiplets, allyl and vinyl group protons; $\delta$=6.80, 6.95, 7.30 and 7.45, quartet, aromatic protons). A solution of 8.0 g 4-allyloxystyrene in 33.0 g toluene was stirred for 5 minutes at room temperature. To this solution was added 0.414 g of a 2% solution of dihydrogen hexachloroplatinate hexahydrate in n-butyl acetate. The resulting solution was then heated to 80° C. and 25.25 g of a difunctional Si—H terminated polydimethylsiloxane resin of molecular weight 1010 was added gradually over 4 hours. At the end of that time, infrared spectroscopy showed that the peak at 2130 cm$^{-1}$ had disappeared indicating complete consumption of the Si—H groups. Solvent was then removed under reduced pressure to yield 33 g of a light brown low viscosity liquid. Reaction of 1 gram of this product with 0.02 grams methanesulfonic acid led to rapid formation of a rubbery gel insoluble in common organic solvents.

EXAMPLE 11

Example 3 was repeated except that no photoinitiator is used and the irradiation time was 1 minute. A slightly yellow film insoluble in chloroform and other common organic solvents was obtained.

EXAMPLE 12

A mixture of 8.0 g 4-allyloxystyrene in 26.57 g toluene was stirred at room temperature for 5 minutes and 0.35 g of a 2% solution of dihydrogen hexachloroplatinate hexahydrate in n-butyl acetate was added. The mixture was then heated to 80° C. and 18.57 g of a heptafunctional Si—H containing polydimethylsiloxane resin of molecular weight 2600 was added over 40 minutes.

Solvent was then removed under reduced pressure to yield 26.76 g of a slightly yellow viscous liquid.

Reaction of 0.5 gram of this product with 0.02 gram methane sulfonic acid led to rapid formation of a reddish brown solid mass.

EXAMPLE 13

An aliquot of the styryloxy silicone resin synthesized in Example 12 was blended with 3% by weight of a commercially available triarylsulfonium salt photoinitiator (UVE-1014, trademark of General Electric). A drop of this formulation was placed on a glass slide and irradiated under a medium-pressure mercury lamp at an intensity of about 100 mw/cm$^2$ at 365 g for 30 seconds. At the end of this time the formulation had completely cured to a tack-free rubbery film. Irradiation for 70 seconds led to formation of a purple rubbery tack-free film.

Further styryloxy resins within the invention include cationically polymerizable resins selected from:

(A) A vinyl polymer having a plurality of groups within the backbone of the formula:

(B) Compounds of the formula:

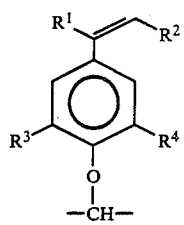

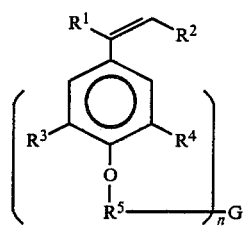

wherein $R^1$ and $R^2$ are H or one of $R^1$ or $R^2$ is H and the other is methyl; $R^3$ and $R^4$ are H, lower alkyl, or alkoxy if $R^2$ is not methyl; $R^5$ is divalent hydrocarbon radical; n is an integer of at least 2 and G is a n-valent organic or inorganic radical free of amine, aliphatic hydroxyl, aliphatic thiol, or other groups which interferewith cationic polymerization wherein G is selected from:

(i) a radical comprising an n-valent polyphosphazene;
(ii) a radical comprising an n-valent polyether; or
(iii) a radical of the formula:

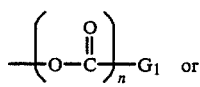 or (iv) a radical of the formula

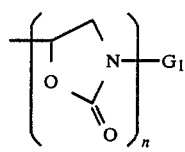

where $G_1$ is any n-valent organic or inorganic radical free of amino, aliphatic hydroxyl, aliphatic thiol, or other groups which interfere with cationic polymerization.

Examples of such further resins follow.

EXAMPLE 14

Vinyl polymer with Styryloxy Groups:

To a mixture of 1.5 equivalents $K_2CO_3$ dispersed in acetone is added 1.1 equivalent p-hydroxybenzaldehyde and sufficient polyvinyl chloride or vinyl chloride copolymer to provide approximately 1 equivalent of allylic chloride groups (i.e. $-CH=CH-CHCl-$). The mixture is refluxed for about 4 hours after which the inorganic salts are filtered and the polymer precipitated with hexane or petroleum ether and dried. The resulting polymer has multiple groups within its backbone of the structure:

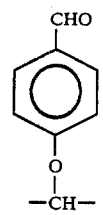

The aldehyde equivalence of the polymer may be determined spectrophotometrically.

The aldehyde containing polymer is then dissolved in tetrahydrofuran (THF) and a Wittig reagent soln, prepared by mixing equimolar amounts of methyltriphenylphosphonium bromide and sodium amide and filtering out the inorganic salts, is added dropwise until an approximately 10% excess of the Wittig reagent has been added.

The mixture is then refluxed for about 4 hours while $N_2$ is bubbled into the mixture. After the solution has been allowed to return to room temperature, methanol is added to precipitate the product. The product is collected dried and identified as a vinyl chloride copolymer having plural groups within its backbone of the formula:

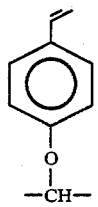

EXAMPLE 15

Two equivalents of the monoethoxylate of 4-hydroxybenzaldehyde is reacted with 1 mole oxalylchloride followed by Wittig reaction on the aldehyde functionalities to give

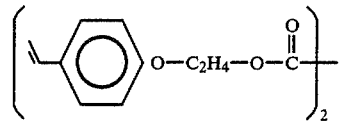

Other di or polyesters may be prepared by analogous procedures, using, for instance, sebacyl chloride, phthalyl chloride, the tetrachloride of benzophenone tetracarboxylic acid, etc., or the corresponding acid anhydrides.

EXAMPLE 16

The monoethoxylate of 4-hydroxybenzaldehyde is esterified with 2-mercapto acetic acid followed by Wittig reaction to give a thiol functional styryloxy ester of the formula:

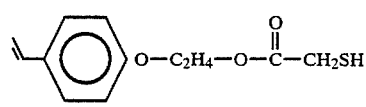

This thiol may then be reacted with a plural functional thiol reactive compound such as a di- or polyisocyanate to give a multifunctional styryloxy resin within the invention.

EXAMPLE 17

4-hydroxy benzaldehyde is reacted with epichlorohydrin in the presence of potassium carbonate as etherification catalyst to give the glycidyl ether of 4-hydroxybenzaldehyde. This ether is polymerized cationically to give a polyether polymer, substantially free of hydroxyls, having repeat units of the formula:

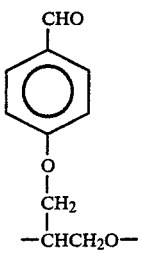

Wittig reaction on this polymer gives the corresponding cationically cureable styryloxy functional polyether.

EXAMPLE 18

The glycidyl ether of 4-hydroxybenzaldehyde is reacted with toluene diisocyanate in the presence of $ZnBr_2/(C_4H_9)_4PO$ catalyst at a ratio of 2 moles aldehyde to each mole diisocyanate under standard oxazolidone synthesis conditions, followed by Wittig reaction to give a cationically polymerizable resin of the formula:

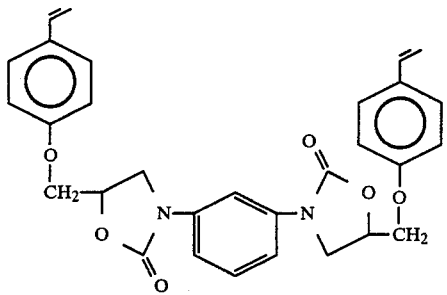

Similar resins can be prepared from other diisocyanate or polyisocyanate functional materials.

EXAMPLE 19

The monoethoxylate of 4-hydroxybenzaldehyde is reacted with a phosphazene polymer or cyclic oligomer having plural repeat units of the formula:

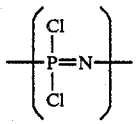

at a ratio of 2 equivalents of aldehyde per repeat unit of the formula above. The reaction is run in THF in the presence of a 10% molar excess (based on aldehyde content) of triethylamine in a sealed tube at 100° C. for 24 hours.

The ammonium chloride produced by the reaction is filtered from the cooled solution and the polymer isolated by evaporation of the solvent. The aldehyde functionality is then subjected to Wittig reaction to give a phosphazene polymer with plural units of the formula:

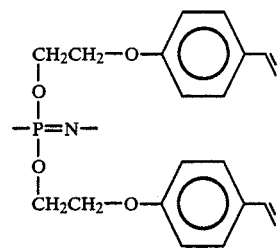

Other products of the invention having phosphazene backbones may also be prepared by methods which will be apparent to those skilled in the art, including copolymers in which some of the P—Cl bonds are substituted with another organic group before reaction with the ethoxylated benzaldehdye. Other benzaldydes may also be used, for instance the monoethylenehydroxy group may be replaced by other alkylene hydroxy groups, the carbon atoms of which may be optionally interrupted with one or more oxygen atoms.

Aldehyde compounds of this type may be represented by the formula:

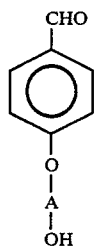

where A is alkylene, alkyleneoxy alkylene or (poly alkyleneoxy) alkylene.

We claim:

1. Cationically polymerizable compounds of the formula:

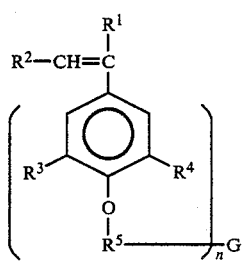

wherein $R^1$ and $R^2$ are H or one of $R^1$ or $R^2$ is H and the other is methyl; $R^3$ and $R^4$ are H, lower alkyl, or alkoxy if $R^2$ is not methyl; $R^5$ is divalent hydrocarbon radical; n is an integer of at least 2 and G is a n-valent organic radical of the formula

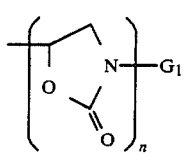
where $G_1$ is the residue of a diisocyanate or polyisocyanate free of amino, aliphatic hydroxyl, or aliphatic thiol, or other groups which interfere with cationic polymerization.
2. A compound as in claim 1, (B) (iv), having the formula:
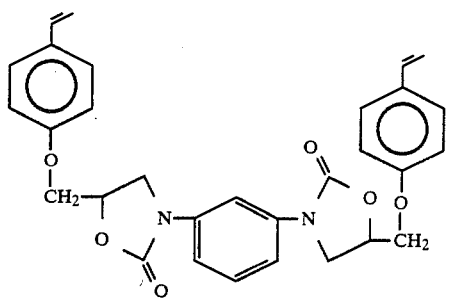
* * * * *